United States Patent [19]

Mannes

[11] Patent Number: 4,585,442
[45] Date of Patent: Apr. 29, 1986

[54] MINIATURE INTRAVENOUS INFUSION RATE CONTROLLER

[75] Inventor: Andrew J. Mannes, Chevy Chase, Md.

[73] Assignee: Ivy Medical, Inc., Minneapolis, Minn.

[21] Appl. No.: 634,645

[22] Filed: Jul. 26, 1984

[51] Int. Cl.[4] .......................................... A61M 5/005
[52] U.S. Cl. ..................... 604/250; 604/34; 604/65; 604/245; 251/7
[58] Field of Search ...................... 604/250, 34, 65–67, 604/245, 251, 253; 417/478; 128/D13; 251/4–10

[56] References Cited

U.S. PATENT DOCUMENTS

| 2,640,675 | 6/1953 | Farris | 251/8 |
| 3,163,176 | 12/1964 | Darling | 604/65 |
| 3,591,219 | 6/1971 | Graziosi | 292/207 |
| 4,312,493 | 1/1982 | Stauffer | 604/250 |
| 4,452,273 | 6/1984 | Hanzana et al. | 604/253 |
| 4,460,358 | 6/1984 | Somerville et al. | 128/D13 |

Primary Examiner—John D. Yasko
Assistant Examiner—Karen L. Kaechele
Attorney, Agent, or Firm—Williamson, Bains, Moore & Hansen

[57] ABSTRACT

An intravenous drip rate control device includes a trough in the rear face of the housing for receiving intravenous tubing. The intravenous tubing is placed within the trough between and in functional communication with a pair of resilient bands. A cam driven by a reversible DC motor moves a lever between a first and second position. In the first position, a blade extending upwardly from the lever is capable of contacting and engaging the tubing and restricting the tubing opening. A tubing door is pivotable about the rear face of the housing between an open and closed position. In the closed position, a plastic material layer extending downwardly from the tubing door contacts and engages the tubing to restrict the tube opening and also provides support for the tubing when the blade applies an upward force on the tubing. The resilient bands ensure minimal "plastic flow" of the tubing and constantly resist the tendency of the side walls of the tubing to extend out and thus the tubing to flatten out.

18 Claims, 6 Drawing Figures

MINIATURE INTRAVENOUS INFUSION RATE CONTROLLER

BACKGROUND OF THE INVENTION

This invention relates to intravenous feed devices, and more particularly to a controller device for controlling the drip rate of intravenous fluid from a gravity feed container.

IV controllers rely on precise regulation of the tubing cross-sectional area for maintaining accurate flow rates. The flow rate is decreased by decreasing the area of the tubing by exerting a pressure on its walls. Control, however, is complicated by the "plastic" properties of the standard IV tubing set as a constant force on the wall of the tubing will cause the tubing to assume a new shape. This can result in cessation of the flow in as little as fifteen minutes. It is therefore further desirable to provide an IV controller which eliminates the problems of "plastic flow" of the tubing under constant force.

Prior art devices have been successfully developed for sensing the drip rate of intravenous fluid from gravity feed containers. In most applications, the controller devices require constant impaction of the tubing. The constant compaction of the tubing by continuous mechanical compression can lead to fatigue problems with the tubing. It is therefore desirable to provide a controller device which can continuously monitor the drip rate of the intravenous fluid, but also to provide a controller device that does not require constant compaction to the tubing.

Calibrating and aligning the controllers during assembly is critical in many prior art controllers. This can lead to costly calibrating procedures during assembling and manufacturing the controllers. It has also been found desirable to provide a drip rate controller which requires no calibration during assembly.

As the controllers will need to be readily portable between hospital or sick rooms, it is desirable to provide a controller assembly which is low-powered and lightweight.

Previous IV controllers had the limitation that they could only operate with either a single type or a limited number of IV tubing. It is desirable therefore to provide an IV controller which can be adapted and used with a wide selection of IV tubings.

It is another general object of this invention to provide an IV controller which is easily and economically manufactured and requires a limited number of working parts.

The present invention is directed toward solving these problems and provides a workable and economical solution to them.

SUMMARY OF THE INVENTION

An intravenous drip rate controller device for use in controlling the drip rate of a solution from an intravenous container mounted on an intravenous pole stand. A drip chamber is connected in fluid flow relation with the intravenous chamber. A flexible elastic drip tube is connected to the drip chamber and extends downwardly therefrom.

The intravenous tubing is placed within a trough in the rear face of the controller housing and between and in functional communication with a pair of resilient bands. These resilient bands act as spring steel as they are fitted on each side of the trough by means of receiving slots.

The controller includes an unbalanced cam which is in rotational engagement with a reversible DC motor. The motion of the cam is capable of raising or lowering a lever which is in communication therewith. The lever is capable of movement between a first and second position. In the first position, a blade extending upwardly from the lever is capable of contacting and engaging the tubing and restricting the flow rate through the tube opening. The blade is not so thin as to cut through the tubing. In the second position, the lever is lowered so that the blade will not pinch or engage the tubing.

The controller also includes a tubing door which includes a downwardly depending flange which may be locked by a slidable door latch. The tubing door is pivotable at one end thereof and capable of movement between a closed and open position. In the closed position, a plastic material layer extending downwardly from the tubing door engages and contacts the tubing aiding in restricting the tube opening and also supporting the tubing upon upward pressure from the blade when the lever is in the first position. In the open position, the tubing door may be swung outwardly from the rear face thereby disengaging the plastic material layer from the tubing.

When the blade and plastic material layer are both disengaged from the tubing, because of the "plastic flow" properties of the IV tubing, the tubing will not immediately revert to its original shape. The resilient bands abutting the sides of the tubing in the trough constantly resist the tendency of the side walls to extend out and therefore of the tubing to flatten out. The bands ensure minimal "plastic flow" of the tubing so that the tubing will immediately revert to its original shape when pressure is released from the blade and plastic material layer.

Other objects and advantages will become apparent from the following detailed description and from the appended drawings in which like numbers have been used to describe like parts of the several views.

DESCRIPTION OF THE PREFERRED EMBODIMENT

Figure 1:
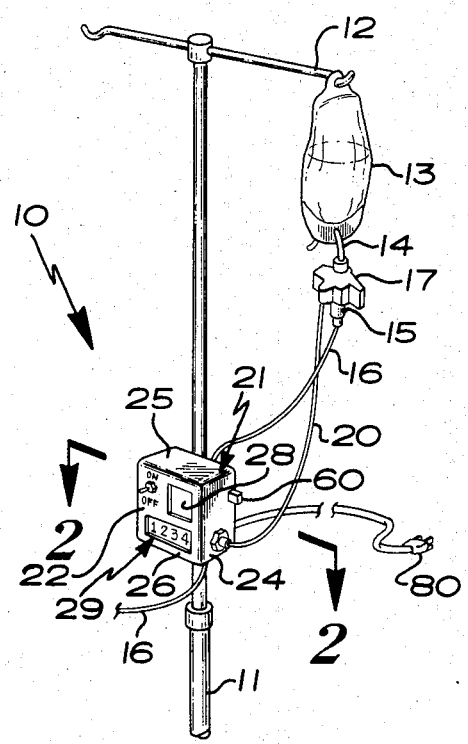
FIG. 1 is a perspective view of the novel drip rate control device mounted on a stand in flow-controlling relation with respect to the drip tube of a gravity feed container.
Figure 4:
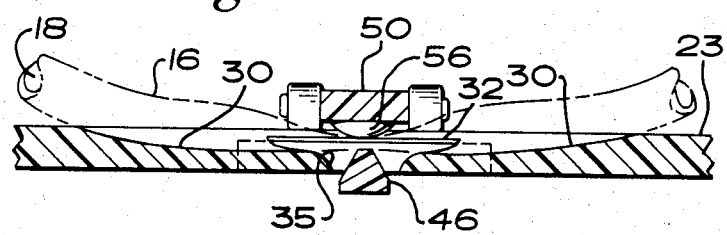
FIG. 4 is a cross-sectional view taken approximately along line 4—4 of FIG. 2 in the direction of the arrows.

Referring now to the drawings, and more particularly to FIG. 1, it will be seen that one embodiment of the novel drip rate controller, designated generally by the reference numeral 10 is thereshown. The controller device 10 is illustrated as being mounted on an intravenous stand 11, intermediate the ends thereof. The IV stand is provided with a transverse bracket 12 at its upper end which supports an IV gravity feed container 13. The IV container 13 is adapted to contain a predetermined amount of intravenous fluid, which is discharged therefrom by action of gravity through a feed tube 14 that projects downwardly from the container. The feed tube 14 is connected in communicating relation with the drip chamber 15 to which is connected the upper end of an elongate drip tube 16. The drip tube 16 infuses the fluid into a patient by an intravenous needle in a well known manner. As shown in FIG. 4, the drip tube 16 has a tube opening 18.

A photoelectric cell reader (drop sensor) 17 is mounted on the drip chamber 15. An electrical conductor cable 20 interconnects the photoelectric cell reader 17 with the controller device 10.

The drip rate controller device 10 includes a housing 21 which is composed of a front wall 22, rear wall 23, substantially parallel vertical side walls 24, top wall 25, and a lower wall 26. The front wall 22 of the housing has a control panel 28 mounted thereon and which also includes a visual light crystal (LCD) display 29.

Figure 3:
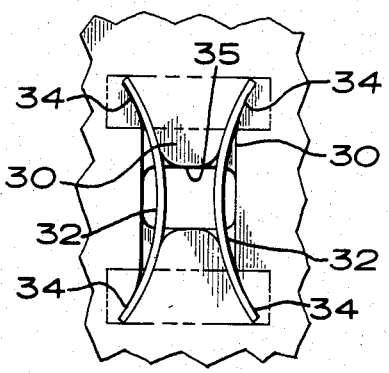
FIG. 3 is a fragmentary enlarged view of the trough and resilient band structure as taken approximately along line 3—3 in FIG. 2 in the direction of the arrows.

As shown in FIGS. 3 and 4, a trough 30 is molded into the rear wall 23. The trough 30 is capable of receiving the tubing 16. Resilient bands 32 are located on each side of the trough 30. The resilient bands 32 are received and retained tightly within the trough 30 by means of receiving slots 34. The receiving slots 34 permit the resilient bands 32 to perform as spring steel. The resilient bands 32 are engageable with both sides of the tubing 16 while the tubing is received by the trough 30.

FIGS. 2, 4, 5, and 6 disclose the clamping means for restricting the tube opening 18. A lever 40 and tubing door 50 are positioned on either side of the rear wall 23 generally parallel to one another. The lever 40 is engageable with an unbalanced cam 42. The unbalanced rotary cam 42 is keyed to an output shaft 43 which is operatively connected to a stepping motor 44 for rotation therewith. The cam 42 is engageable with the lever 40 at one end thereof and provides pivotal movement for the lever 40. The lever 40 is pivoted about lever pivot point 47 at the opposite end of the lever 40. Adjacent the lever pivot point 47 along the lever 40 is an upwardly extending blade 46.

Figure 2:
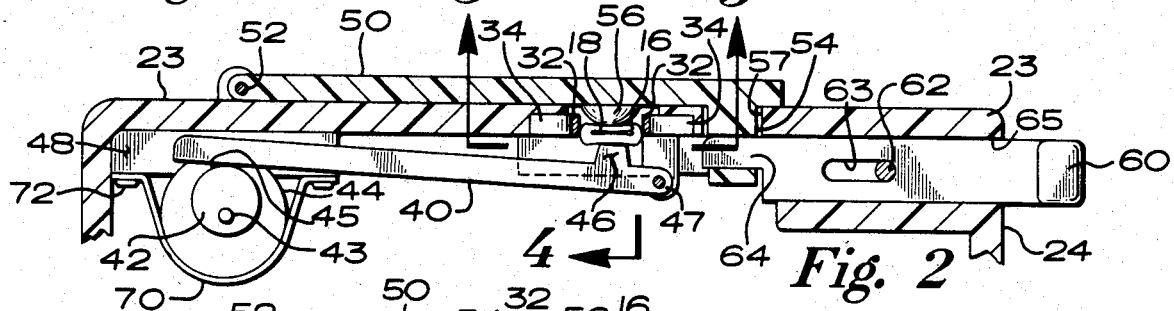
FIG. 2 is a cross-sectional view taken approximately along line 2—2 of FIG. 1 in the direction of the arrows.
Figure 6:
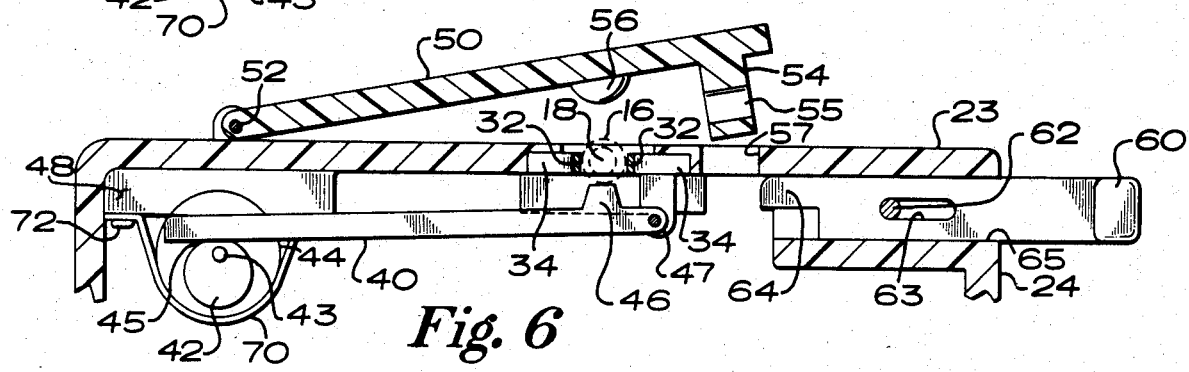
FIG. 6 is a cross-sectional top view illustrating the tubing door in the open position and the lever in its first position with the blade and plastic material layer disengaged from the tubing.

The lever is displaceable between a first position, as shown in FIGS. 2 and 4, and a second position as shown in FIG. 6. In the first position, the cam 42 is in an upward position which forces the lever 40 upward at point 45 and subsequently because of pivoting about pivot point 47, the blade 46 moves upwardly contacting the bottom of tubing 16. When the blade 46 contacts the tubing 16, the tube opening 18 is restricted as shown in FIG. 2. FIG. 6 illustrates the second position of the lever 40. In the second position, the cam 42 is its downward position with the shaft 43 rotating at the upper end of the cam 42. This permits the lever 40 to be lowered about pivot point 47 and thereby lowers the blade 46. In the second position, the blade 46 does not engage or contact the tubing 16 and upward pressure is released on the bottom of the tubing 16. A slot 35 extends through housing rear wall 23 into trough 30; and blade 46 engages tubing 16 through slot 35.

The blade 46 should preferably be as thin as possible, approximately 1/32nd of an inch to lessen the surface area of tubing contact. The blade 46 should not be too thin so that it could cut through the tubing 16. The blade 46 should preferably be made of a plastic or Plexiglas material.

A tubing door or bar 50 is swingably mounted along the rear wall 23 of housing 21 about pivot point 52 at one end thereof. A downwardly depending flange 54 extends downwardly from the lever 50 at the opposite end of the lever 50 from pivot point 52. The downwardly depending flange is capable of locking engagement with door latch 60 by means of flange opening 55.

Figure 5:
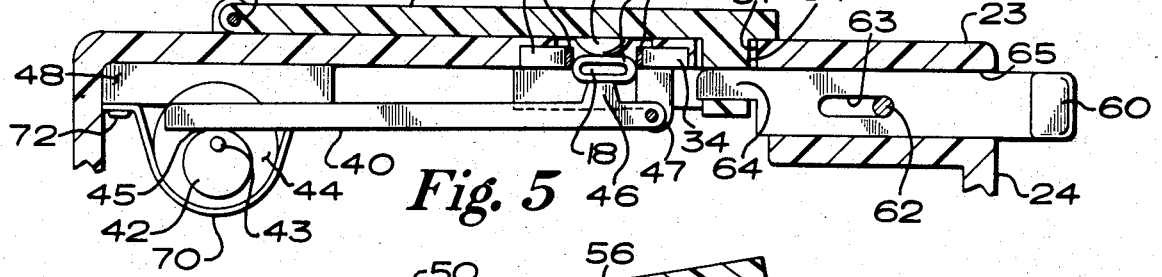
FIG. 5 is a cross-sectional top view illustrating the tubing door in the closed position and the lever in its second position.

The door latch 60 provides for a means for locking the downwardly depending flange 54 and is positioned through the side wall 24 generally parallel and adjacent to the rear face 23. The door latch 60 is capable of moving between a forward and rearward position by sliding within a door latch channel 65. The door latch 60 is capable of locking in its forward or rearward position by means of lock pin 62. A pin opening 63 receives and retains the lock pin 62 therethrough. The forward position of the door latch 60 is shown in FIGS. 2 and 5 and the rearward position is shown in FIG. 6. The forward edge 64 of the door latch is capable of being received and retained in the flange opening 55 of the tubing door 50.

The tubing door 50 also carries a plastic material layer 56 in the shape of a hemispherical protrusion which extends downwardly therefrom between tubing door pivot point 52 and a downwardly depending flange 54. The plastic material layer 52 is aligned along the tubing door 50 so that it is capable of contacting the tubing 16. The plastic material layer 52 is preferably a thin coating of silicone to permit lower tolerances during manufacturing.

The tubing door 50 is capable of pivotal movement between a closed position, as shown in FIGS. 2 and 5, and an open position, as shown in FIG. 6. In the closed position, the tubing door is generally parallel and adjacent to the rear face 23 of the housing 21. The downwardly depending flange 54 is inserted through the rear face opening 57 and the forward edge 64 of the latch 60 is inserted into the flange opening 55 to thereby lock the tubing door in its closed position. As shown in FIG. 2, when the tubing door 50 is in its closed position, the plastic material layer 56 is in position to pinch and contact the top of the tubing 16 and restricts the tube opening 18 in cooperation with blade 46 to restrict the flow rate through the tubing. In the open position, the door latch 60 is slid into its rearward position thereby disengaging forward edge 64 from the flange opening 55 in the downwardly depending flange 54. The tubing door 50 is pivoted away from the rear face 23 of the housing 21 thereby disengaging plastic material layer 56 from the tubing 16 and permitting the tube central passage 18 to assume its normal, fully open shape as shown in FIG. 6.

As shown in FIG. 4, the lever 40 in its first position having the blade 46 engaging the bottom side of the tubing 16 and the tubing door 50 being in its closed position and having the plastic material layer 56 engaging the top of tubing 16 cooperate to restrict the tube opening 18. FIG. 5 is an intermediate step in regulating the flow rate through tube opening 18. The unbalanced cam 42 is in its downwardly rotated position thereby lowering the lever 40 at point 45 which in turn lowers the blade 46 and releases its pressure upon tubing 16. The tube opening 18 enlarges in such an intermediate position. In FIG. 6, the lever 40 in the second position having blade 46 lowered away from the tubing 16 and the tubing door 50 in its open position having the plastic material layer 56 disengaged from the tubing 16 to allow the tube 16 to be released from the controller device 10.

Experimentation has shown that the tubing will not immediately revert to its original shape when the lever 40 is in its second or released position. To alleviate this problem, a slight restoring force is applied to the side of the tubing 16. A pair of resilient bands 32 are inserted on either side of the trough 30 through which the tubing 16 is inserted. As shown in FIG. 3, the resilient bands 32 are inserted in receiving slots 34 which allow the resilient bands 32 to function as spring steel. These bands 32 ensure minimal "plastic flow," as the resilient bands 32 constantly flex to resist the tendency of the side walls of the tubing 16 to extend out and the tubing 16 to flatten out. When the blade 46 and the plastic material layer 56 pressure are reduced, the resilient bands 32 spring back in on the side walls of the tubing 16 and force the tubing to return immediately to its previous shape. The resilient bands 32 provide constant, resilient resistance to the spreading or flattening of the IV tubing by their restraining effects.

By using the pivotal lever 40, a minimal mechanical force through cam 42 on one end of lever 40 is required to provide the compression required of the tubing 16 to achieve the flow restriction desired. The mechanical advantage of this cam and lever arrangement is approximately 9 to 1. Hence, less power is required and a smaller motor may be used thereby reducing the weight and size of the entire controller 10. The mechanical gain refers to the ratio of the distance of the cam to the pivot 45 axis versus the IV tubing to that axis.

The motor 44 is secured to a mounting block 48 by means of fasteners 72. An electrical cord plug 80 is provided for electrical connection of the IV controller 10 with an ordinary 110 volt electrical outlet.

In operation, the operator will actuate the on-off switch to energize the circuitry for the drip rate controller device. The operator will then position the tubing 16 within the trough 30 in the rear face 23 of the housing 21 and close door 50 to the tube containing position shown in FIG. 5. The door latch 60 is then slidably inserted into its forward position by having its forward edge 64 inserted into the flange opening 55 of the tubing door 50. In the tubing door 50 closed position, the plastic material layer 56 will engage the top of the tubing 16. In the trough 30, the tubing 16 should be placed between and in communicating relation with the resilient bands 32. The plastic material layer 56 also provides rigid support for the tubing 16 against the force exerted by blade 46 upon the tubing 16. The position of lever 40 is controlled by the rotation of the cam 42 connected to the shaft of the reversible DC motor 44. When it is desired to restrict the tube opening 18, the unbalanced cam 42 is rotated in an upward position as shown in FIG. 2 at point 45 thereby causing the blade 46 to more tightly engage the tubing 16. The blade 46 engaging the tubing 16 and the plastic material layer 56 engaging the tubing 16 cooperate to restrict the tube opening 18 to reduce fluid flow.

When it is desired to increase the flow rate, the unbalanced cam 42 is rotated to its downwards position at point 45 as shown in FIG. 6 thereby lowering the lever 40 and the pressure that blade 46 applies on the tubing 16. The tubing 16 is allowed to revert to its original shape by means of the resilient bands 32 which are positioned on either side of the tubing 16 and constantly resist the tendency of the side walls of the tubing to extend out.

Automatic drip rate control can be achieved by utilizing signals from drip rate sensor 17 to actuate reversible motor 44. The motor will be controlled in such a way as to rotate cam 42 to the position shown in FIG. 2 when the sensor indicates that the drip rate is too high, so as to restrict tube 16. An excessively low drip rate would actuate motor 44 to rotate cam 42 to the position shown in FIG. 5 to release lever pressure on tube 16. Manual operation can also be utilized by providing on/off or directional drive switches on housing 21 for cam motor 44. Upon visual observation of an unacceptably high drip rate, the operator would actuate a switch on the controller 10 to rotate cam 42 to the position shown in FIG. 2 to increase the restrictive pressure of lever blade 46 on tube 16. The opposite procedure would be utilized to further open tube 16 to increase the drip rate by actuating motor 44 to rotate cam 42 to the position shown in FIG. 5.

When the operator does not desire to obtain flow regulation by means of the control device 10, the door latch 60 is slid to its rearward position and forward edge 64 is released from latch opening 55. The operator then releases the downwardly depending flange 54 of the tubing door 50 from the opening 57 and the tubing door 50 is pivoted away from the rear face 23 thereby disengaging the plastic material layer 56 from the tubing 16.

While the preferred embodiments of the present invention have been described, it should be understood that various changes, adaptions, and modifications may be made therein without departing from the spirit of the invention and the scope of the appended claims.

What is claimed is:

1. An intravenous drip rate controller device for use in controlling the drip rate of a solution from an intravenous container mounted on an intravenous pole stand and having a drip chamber connected in fluid flow relation with said intravenous container, a flexible elastic drip tube connected to the drip chamber and extending downwardly therefrom for transporting a solution through the continuous opening in said tube, and a drip rate sensing means positioned in proximity to the drip chamber for sensing each intravenous drip and generating an electrical signal in response to each drip indicative of the drip rate, said device comprising:

a trough receiving said tube;

a lever pivotable at one end thereof and engageable at the other end with a cam, said cam being in rotational engagement with a motor actuated by electrical signals from said drip rate sensing means, and said lever including a blade which is engageable with one side of said tube in said trough;

a tubing door pivotable at one end and having a plastic material layer projecting therefrom for engagement with the other side of said tube opposite said blade;

a means for locking said door in a closed position over said trough wherein said plastic material layer may engage said tube; and resilient band located on each side of said trough and engageable with opposed side walls of said tube at locations thereon where said tube would tend to distend in response to the squeezing action of said lever and said door to apply a restoring force to the sides of said tube when the pressure of said blade and door on said tube is reduced.

2. The intravenous drip rate controller device of claim 1 wherein:

said lever is displaceable by said cam between a first position, wherein said cam forces said lever towards said trough and urges said blade into engagement with said tubing to restrict said tube opening, and a second position, wherein said lever follows said cam away from said trough and said blade moves in a direction away from said tubing thereby decreasing the pressure applied on said tubing by said blade.

3. The intravenous drip rate controller device of claim 1 wherein:

said trough has a slot through one side thereof and said blade engages said tubing through said slot.

4. The intravenous drip rate controller device of claim 1 wherein:

said means for locking said door comprises a flange depending from one side of said door, an opening in said flange, and a slidable bar, said slidable bar being movable between a forward position, wherein said flange opening receives and retains said slidable bar, and a rearward position, wherein said slidable bar is removed from said flange opening.

5. The intravenous drip rate controller device of claim 4 wherein:

said tubing door is movable between said closed position, wherein said downwardly depending flange is locked by said slidable bar forcing said plastic material layer to contact said tubing and restrict said tube opening, and an open position, wherein said downwardly depending flange is released from said slidable bar and said tubing door is swung away from said trough so that said plastic material layer disengages said tubing.

6. The intravenous drip rate controller device of claim 4 wherein:

said slidable bar includes a pin opening, said pin opening receiving and retaining a lock pin therethrough which facilitates the locking of said slidable bar in its forward and rearward positions.

7. The intravenous drip rate controller device of claim 1 wherein:

said resilient bands are received and retained tightly by receiving slots, said resilient bands negating the effects of plastic flow and allowing said tubing to return immediately to its original shape when said plastic material layer and said blade disengage said tubing for greater flow.

8. The intravenous drip rate controller device of claim 1 wherein:

said lever has a mechanical advantage of nine to one allowing a minimum mechanical force to be required to provide the pressure required on said tubing to achieve the flow restriction desired.

9. An intravenous drip rate controller device for use in controlling the drip rate of a solution from an intravenous container mounted on an intravenous pole stand and having a drip chamber connected in fluid flow relation with said intravenous container, a flexible drip tube connected to said drip chamber and extending downwardly therefrom for delivering a solution to a patient through the continuous opening in said tube, and a drip rate sensing means positioned in proximity to the drip chamber for sensing each intravenous drip and generating an electrical signal in response to each drip indicative of the drip rate, said device comprising:

a housing;

a trough positioned along said housing for receiving said tube;

a lever pivotable at one end thereof and engageable at the other end with a cam, said cam being in rotational engagement with a motor, said lever including a blade extending upwardly which is engageable with said tube, said lever being displaceable between a first position, wherein said cam is in a position forcing said lever towards said trough and said blade into engagement with said tube to restrict said tube opening, and a second position, wherein said cam is in a position carrying said lever and said blade away from said trough, thereby decreasing the pressure applied on said tube by said blade and increasing the area of said tube opening;

a tubing door pivotable at one end, said tubing door having a plastic material layer extending from said door and engageable with said tube when said door is in a closed position over said trough;

means for locking said door in said closed position;

said tubing door being displaceable between said closed position, wherein said tubing door closely abuts said housing forcing said plastic material layer to engage said tube and restrict said tube opening, and an open position, wherein said door is released from said locking means and said tubing door is swung away from said housing so that said plastic material layer disengages said tube; and resilient bands located on each side of said trough and engageable with opposed side walls of said tube at locations thereon where said tube would tend to distend in response to the squeezing action of said lever and said door to thereby negate the effects of plastic flow and allowing said tube to return to its original shape when said plastic material layer and said blade disengage said tube for greater flow.

10. The intravenous drip rate controller of claim 9 wherein:

said means for locking said tubing door comprises an apertured flange depending from said door for receiving and retaining a slidable bar, said slidable bar being capable of movement between a forward position, wherein said flange aperture receives and retains said slidable bar, and a rearward position, wherein said slidable bar is removed from said flange aperture.

11. The intravenous drip rate controller device of claim 9 wherein:

said resilient bands cooperate with said blade in its first position and said plastic material layer in the closed position of said door to restrict said tube opening and decrease the flow rate.

12. The intravenous drip rate controller device of claim 9 wherein:

said resilient bands are received and retained tightly by receiving slots.

13. An intravenous drip rate control device for use in controlling the drip rate of a solution from an intravenous container mounted at an elevated level, and having a drip chamber connected in fluid flow relation with said container and a drip tube connected to the drip chamber for directing a solution to a patient through the continuous opening in said tube, said device comprising:

wall means mounting a clamping assembly for selective clamping engagement with said tube to regulate the restriction of said continuous opening in said tube;

a slot in said wall means along which said drip tube is positioned;

said clamping assembly comprising a lever pivotally mounted on one side of said wall means and carrying a contact element movable into engagement with one side of said tube in said slot when said lever is pivoted towards said slot, and a tube door pivotally mounted on the side of said wall means and swingable to a closed position over said slot for engagement with the opposite side of said tube to act as a backing support for said drip tube, whereby with said tube lying in said slot and said door in said closed position, said continuous opening in said tube may be restricted to reduce the rate of flow of intravenous solution therethrough by pivotally moving said lever towards said slot to squeeze said tube between said contact element and said door; and a resilient member located on each side of said slot positioned to resiliently engage opposite sides of said drip tube, to apply an inward restoring force to the sides of said tube in a direction generally at right angles to the direction of clamping force applied by said lever contact element and at locations against said side walls of said tube where said tube would tend to distend in response to the squeezing action of said lever and said door, when the squeezing pressure of said contact element on said tube is reduced.

14. The intravenous drip feed controller device of claim 13 wherein:

a layer of plastic material having a measure of resiliency is carried on said door at a location thereon where it will engage said drip tube when said door is in said closed position.

15. The intravenous drip feed controller device of claim 13 wherein:

said clamping assembly further comprises means for locking said door in said closed position.

16. The intravenous drip feed controller device of claim 13, and further including:

a cam drivingly connected to a motor for rotary movement, said cam being positioned to engage said lever as a cam follower adjacent one end of said lever remote from the pivotal mounting of said lever, and said lever being displaceable by said cam between a first position wherein said lever is moved towards said slot and said contact element is brought into engagement with said tube and a second position wherein said lever follows said cam away from said slot and said contact element moves in a direction away from said tube to thereby decrease the pressure applied to said tube and increase the size of said continuous opening in said tube.

17. The intravenous drip feed controller device of claim 13 wherein:

said lever contact element has a blunt contact surface for engaging said one side of said tube and said door carries a blunt contact member for engaging said opposite side of said tube, whereby said tube will tend to be flattened out and distended by the clamping action of said lever and said door and to extend laterally towards said resilient members in said right angle direction.

18. The intravenous drip feed controller device of claim 13 wherein:

said resilient members comprise bowed bands having free ends secured in place and bowed central segments in contact with said two side walls of said tube at said force restoring locations thereon.

* * * * *